United States Patent
Yeon et al.

[11] Patent Number: 5,484,785
[45] Date of Patent: Jan. 16, 1996

[54] SALTS OF A QUINOLONE-CARBOXYLIC ACID

[75] Inventors: Kyu J. Yeon, Seoul; Je H. Kim, Kyonggi; Kyung E. Choi, Seoul; Dal H. Kim, Kyonggi; Ki H. Lee, Seoul, all of Rep. of Korea

[73] Assignee: Cheil Foods & Chemicals, Inc., Seoul, Rep. of Korea

[21] Appl. No.: 256,725

[22] PCT Filed: Jan. 21, 1993

[86] PCT No.: PCT/KR93/00006

§ 371 Date: Aug. 26, 1994

§ 102(e) Date: Aug. 26, 1994

[87] PCT Pub. No.: WO93/14068

PCT Pub. Date: Jul. 22, 1993

[30] Foreign Application Priority Data

Jan. 21, 1992 [KR] Rep. of Korea .................. 92-794

[51] Int. Cl.⁶ .................. A61K 31/495; C07D 401/10
[52] U.S. Cl. .................. 514/254; 544/363
[58] Field of Search .................. 544/365; 514/254

[56] References Cited

U.S. PATENT DOCUMENTS 4,705,789  11/1987  Grohe et al. .................. 514/254
4,772,605  9/1988   Naik et al. .................. 514/254
4,957,922  9/1990   Lammens et al. .................. 514/255

FOREIGN PATENT DOCUMENTS 0067666  12/1982  European Pat. Off. .
155006   9/1985   European Pat. Off. .

*Primary Examiner*—Emily Bernhardt
*Attorney, Agent, or Firm*—Burns, Doane, Swecker & Mathis

[57] ABSTRACT

The present invention provides novel organic acid addition salts of a quinolone-carboxylic acid of formula (I)

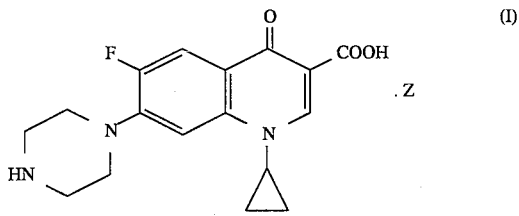

wherein Z is 5-oxotetrahydrofuran-2-carboxylic acid or 2-hydroxyglutaric acid. The salts are highly soluble in water and are thus suitable to prepare a stable injection in storage for a long period of time.

3 Claims, 1 Drawing Sheet

SALTS OF A QUINOLONE-CARBOXYLIC ACID

TECHNICAL FIELD

This application is a 371 of PCT/KR93/00006 filed Jan. 21, 1993.

The present invention relates to novel organic acid addition salts of a quinolone-carboxylic acid and a process for preparing the same. More particularly, the present invention concerns 1-cyclopropyl-6-fluoro-1,4-dihydro-4-oxo- 7-(1-piperazinyl)-quinoline-3-carboxylic acid 5-oxotetrahydrofuran-2-carboxylate or 2-hydroxyglutarate, which is highly soluble in water giving an injectable solution, its preparation, and use in treating infectious diseases caused by bacteria.

BACKGROUND ART

The following quinolone-carboxylic acid of the formula:

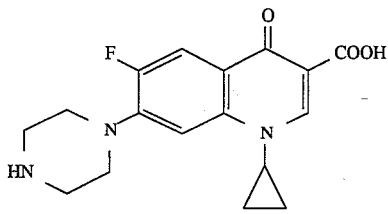

is known in the art as having potent antibacterial activities. This compound, 1-cyclopropyl-6-fluoro-1,4-dihydro-4-oxo-7-(1-piperazinyl)-quinoline-3-carboxylic acid, generally called "Ciprofloxacin" (hereinafter, referred to as "Ciprofloxacin") has been widely used for the treatment of infectious diseases in mammal caused by bacteria. See, P. B. Fernandes ed., International Symposium on Quinolones, pp. 1–134, J. R. Porous, S. A., Barcelona, Spain (1989).

Although Ciprofloxacin is very active in treating bacterial disease, the compound has certain disadvantages in that it is almost insoluble or sparingly soluble in water. This property bars the compound from formulating it into injectable solutions.

Aiming at overcoming these disadvantages, various acid and base addition salts of Ciprofloxacin have been developed, which can easily dissolve in water to a desired extent and do not cause occurrence of precipitation in the resulting solution during storage. For example, U.S. Pat. No. 4,705,789 to Grohe et al. discloses that hydrochloride, methanesulfonate, acetate, propionate, succinate and lactate of Ciprofloxacin are suitable to prepare highly stable injectables. These salts, however, cause some problems from the pharmaceutical point of view. That is, Ciprofloxacin hydrochloride is unstable in solution; methanesulfonate exhibits a very low value of pH; and acetate and propionate smell unpleasant. Ciprofloxacin lactate tends to occur precipitation in an injection when it is contained in the injection in an excessive amount.

European Patent Publication No. 0 067 666 A1 suggests to use galacturonic acid, aspartic acid, glutamic acid and gluconic acid as an acid for forming salts with Norfloxacin or Enoxacin which do not cause such precipitation in solution. The salts formed by adding these acids are proven to be pharmaceutically valuable.

German Patent Application Nos. P35 00 243.3 and P35 17 709.8 disclose sodium hydroxide, potassium hydroxide, ethanolamine, lysine, N-methyl glucamine and arginine as the bases which can form non-precipitating salts with Ciprofloxacin. However, an aqueous solution of each salt derived from those bases is not suitable to be administered parenterally owing to its high pH value.

DISCLOSURE OF THE INVENTION

According to the present invention, it has been surprisingly discovered that the solubility of Ciprofloxacin in water can be significantly enhanced by reacting it with certain organic acids, that is, 5-oxotetrahydrofuran-2-carboxylic acid or 2-hydroxyglutaric acid to give a novel salt thereof.

It is therefore an object of the invention to provide a novel salt of Ciprofloxacin which can easily dissolve in water resulting in highly stable injections without causing precipitation, even after a long-term period of storage.

It is another object of the invention to provide a process for preparing novel salts of Ciprofloxacin.

It is still another object of the invention to provide a pharmaceutical composition comprising the novel salt of the invention as an active ingredient.

It is still further object of the invention to provide a method for treating bacterial diseases by the novel salt of the invention.

Any additional objects of the invention will become apparent through reading the remainder of the specification.

According to the present invention, a novel compound is provided which is represented by the formula:

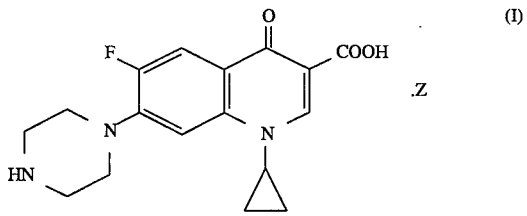

wherein, Z is 5-oxotetrahydrofuran-2-carboxylic acid or 2-hydroxyglutaric acid.

The compound according to the invention is prepared by reacting Ciprofloxacin with 5-oxotetrahydrofuran-2-carboxylic acid or 2-hydroxyglutaric acid. 2-Hydroxyglutaric acid may be easily convertible from 5-oxotetrahydrofuran-2-carboxylic acid in an aqueous solution and vice versa. The organic acid addition salts of Ciprofloxacin prepared according to the invention exhibit considerably higher solubility than that of other conventional salts. The pH of a solution of the salts of the invention in water ranges from 4 to 5 which may be used as injectable solutions in its entirety.

5-Oxotetrahydrofuran-2-carboxylic acid or 2-hydroxyglutaric acid used in the present invention can be present in either of their optical isomer forms, such as (R)- and (S)-forms, or racemic forms; thus, the compound of the invention may also be in (R)- or (S)- forms, or racemic forms.

In another aspect, the present invention provides a pharmaceutical composition for use in treating infectious diseases in mammal caused by bacteria, which contains the compound of the formula (I) as an active ingredient.

The pharmaceutical composition of the invention can be prepared in solution by dissolving the compound of the formula (I) in deionized water. Alternatively, the composition can be prepared in solution by dissolving Ciprofloxacin and 5-oxotetrahydrofuran-2-carboxylic acid or 2-hydroxyglutaric acid in deionized water separately or simultaneously until complete dissolution.

3

The organic acid, namely, 5-oxotetrahydrofuran-2-carboxylic acid or 2-hydroxyglutaric acid, can be present in the resulting compositions preferably in an amount of 0.01 to 10% by weight, more preferably 0.01 to 3% by weight.

If necessary, saline, or an acidic or alkaline solution such as an aqueous solution of sodium hydroxide can be further added to adjust the concentration of the active ingredient and pH of the resulting solution. The pharmaceutical composition may also contain conventional ingredients, such as an isotonizing agent, a thickener, an absorption-accelerator, an absorption-inhibitor, a crystallization-inhibitor, a complexing agent, an antioxidant, a hydrating agent, and the like.

The pharmaceutical composition of the invention may be formulated in parenteral dosage unit forms. Preferably, parenteral solutions are used which are packaged in ampoules, injectable vials, injectable bottles, plastic bags, and so forth. Also, concentrate or powder forms may be used. In addition, the pharmaceutical composition of the invention may be formulated into non-parenteral dosage forms, such as tablets, capsules, lozenges, pills, oral solutions and suspensions, suppositories, and the like.

In still another aspect, the present invention provides a method for treating infectious diseases caused by bacteria which comprises administering the compound of the formula (I) to the patient in need of such treatment.

The compound of the invention is preferably administered parenterally, with a dosage adjusted to the needs and tolerances of the individual patient. The usual mammalian dosage range for a 70 kg human subject is from 70 mg to 500 mg per day, preferably from 100 mg to 400 mg per day, optionally in divided portions.

BEST MODE FOR CARRYING OUT THE INVENTION

Figure 1:
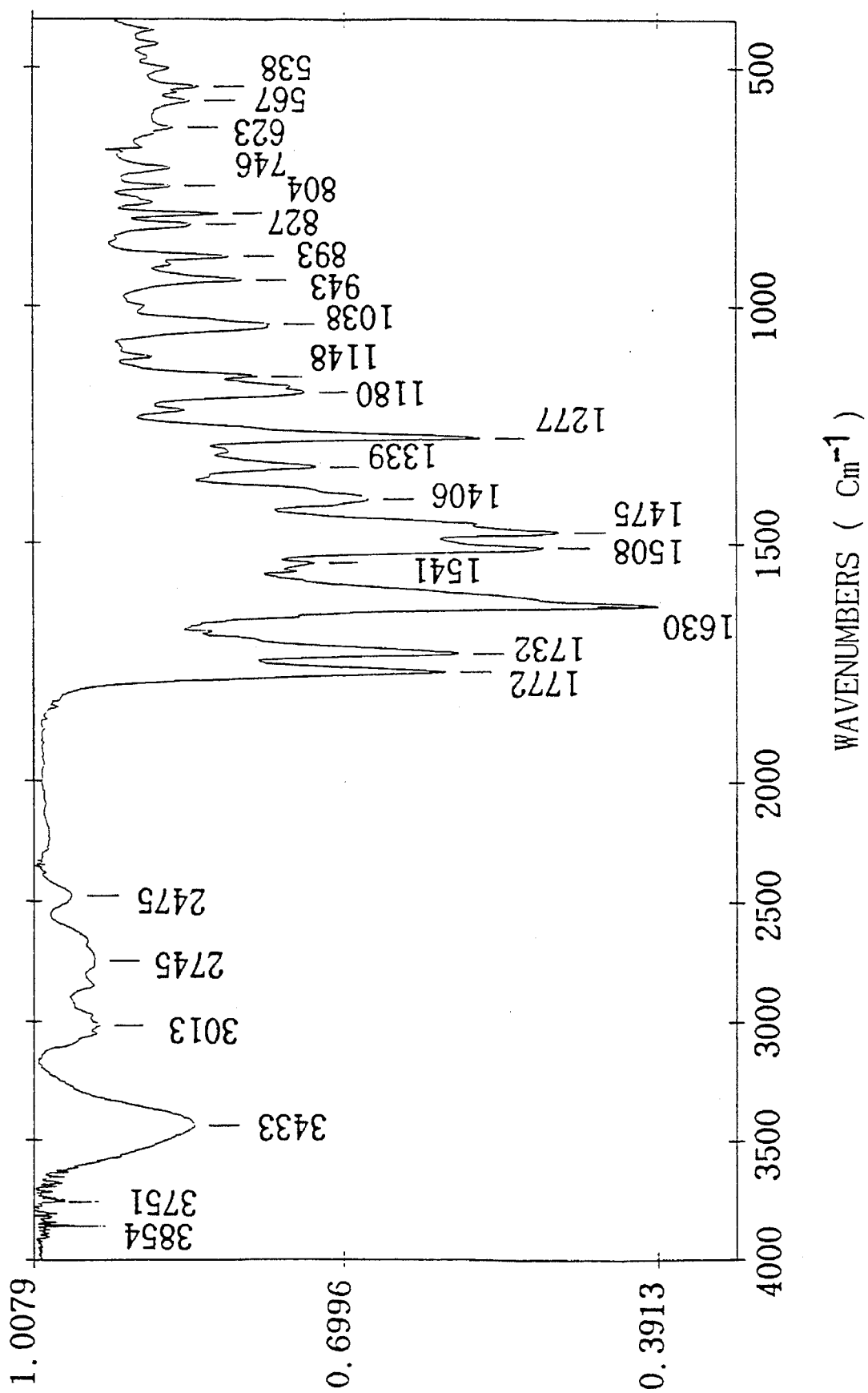
FIG. 1 represents an IR spectrum for (S)-5-oxotetrahydrofuran-2-carboxylic acid addition salt of Ciprofloxacin.

The present invention will be illustrated in greater detail by way of the following examples. The examples are presented for illustration purpose only and should not be construed as limiting the invention which is properly delineated in the claims.

EXAMPLE 1

Preparation of Ciprofloxacin (S)-5-Oxotetrahydrofuran-2-carboxylate 0.781 G (0.006 mole) of (S)-5-oxotetrahydrofuran-2-carboxylic acid and 1.99 g (0.006 mole) of Ciprofloxacin were added to 10 mL of distilled water. The resulting mixture was stirred for 30 minutes to dissolve it completely. After adding 20 mL of anhydrous acetone, the resulting solution was further stirred for 30 minutes under ice-cooling and allowed to stand to precipitate solids. The precipitated solids were filtered under reduced pressure through a filter paper (Whatman Filter Paper No. 1), washed three times with each 30 mL of anhydrous acetone, and dried under vacuum to give 2.27 g of the titled compound as white solids. M.P. 214°–219° C. (decomposition) $[\alpha]D^{25}=-3.33$ ($H_2O$)

A quantitative analysis showed that the salt thus obtained contained 0.342 mole of water per mole of the salt.

IR (KBr, $cm^{-1}$): 1630, 1732, 1772, 3433. (See, FIG. 1)

4

EXAMPLE 2

Preparation of Ciprofloxacin (R)-5-Oxotetrahydrofuran-2-carboxylate 0.781 G (0.006 mole) of (R)-5-oxotetrahydrofuran-2-carboxylic acid and 1.99 g (0.006 mole) of Ciprofloxacin were added to 10 mL of distilled water. The resulting mixture was stirred for 30 minutes to dissolve it completely. After adding 20 mL of anhydrous acetone, the resulting solution was further stirred for 30 minutes under ice-cooling and allowed to stand to precipitate solids. The precipitated solids were filtered under reduced pressure through a filter paper (Whatman Filter Paper No. 1), washed three times with each 30 mL of anhydrous acetone, and dried under vacuum to give 2.33 g of the titled compound as white solids. M.P. 211–212° C. (decomposition) $[\alpha]D^{25}=+4.72$ ($H_2O$)

A quantitative analysis showed that the salt thus obtained contained 0.454 mole of water per mole of the salt.

IR (KBr, $cm^{-1}$): 1630, 1732, 1772, 3433.

EXAMPLE 3

Preparation of Ciprofloxacin racemic 5-Oxotetrahydrofuran-2-carboxylate 0.781 G (0.006 mole) of racemic 5-oxotetrahydrofuran-2-carboxylic acid and 1.99 g (0.006 mole) of Ciprofloxacin were added to 10 mL of distilled water. The resulting mixture was stirred for 30 minutes to dissolve it completely. After adding 20 mL of anhydrous acetone, the resulting solution was further stirred for 30 minutes under ice-cooling and allowed to stand to precipitate solids. The precipitated solids were filtered under reduced pressure through a filter paper (Whatman Filter Paper No. 1), washed three times with each 30 mL of anhydrous acetone, and dried under vacuum to give 2.34 g of the titled compound as white solids. M.P. 211°–212° C. (decomposition)

A quantitative analysis showed that the salt thus obtained contained 0.335 mole of water per mole of the salt.

IR (KBr, $cm^{-1}$): 1630, 1732, 1772, 3433.

EXAMPLE 4

Preparation of an Aqueous Solution of Ciprofloxacin 5-Oxotetrahydrofuran-2-carboxylate 1.393 G (corresponding to 1 g of Ciprofloxacin) of each salt obtained in Examples 1–3 was dissolved in water to a 10 mL volume. An adequate amount of sodium chloride was added to the resulting solution to make it isotonic. The isotonic solution was diluted with saline to give a solution containing the salt as an active ingredient in the concentration of 1% (calculated in terms of Ciprofloxacin). The solution thus obtained was adjusted to pH 4.3 with a 2N sodium hydroxide or 2N hydrochloric acid solution.

EXAMPLE 5

Preparation of an Aqueous Solution of Ciprofloxacin 5-Oxotetrahydrofuran-2-carboxylate Each Salt obtained in Examples 1–3 was dissolved in water to give a 10% Ciprofloxacin solution. An adequate amount of sodium chloride was added to the resulting solution to make it isotonic. The isotonic solution was diluted with saline to give a solution containing the salt as an active ingredient in the concentration of 0.4% (calculated in terms of Ciprofloxacin). The solution thus obtained was adjusted to pH 4.3 with a 2N sodium hydroxide or 2N hydrochloric acid solution.

EXAMPLE 6

Preparation of an Aqueous Solution of Ciprofloxacin 5-Oxotetrahydrofuran-2-carboxylate Each salt obtained in Examples 1–3 was dissolved in water to give a 10% Ciprofloxacin solution. An adequate amount of sodium chloride was added to the resulting solution to make it isotonic. The isotonic solution was diluted with saline to give a solution containing the salt as an active ingredient in the concentration of 0.2% (calculated in terms of Ciprofloxacin). The solution thus obtained was adjusted to pH 4.3 with a 2N sodium hydroxide or 2N hydrochloric acid solution.

EXAMPLE 7

An aqueous solution of Ciprofloxacin 5-oxotetrahydrofuran-2-carboxylate was directly prepared from the following ingredients by repeating the same procedures as described in Example 4.

| | |
|---|---|
| Ciprofloxacin | 50.0 g |
| 5-Oxotetrahydrofuran-2-carboxylic acid | 1.963 g |
| Sodium chloride | qs. |
| Water | to 200 mL |

The pH of the diluted solution was adjusted to 4.5 with a 2N sodium hydroxide solution.

EXAMPLE 8

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 50.0 g |
| 5-Oxotetrahydrofuran-2-carboxylic acid | 20.0 g |
| Sodium chloride | qs. |
| Water | to 1000 mL |

The pH of the diluted solution was adjusted to 4.5 with a 2N sodium hydroxide solution.

EXAMPLE 9

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 50.0 g |
| 5-Oxotetrahydrofuran-2-carboxylic acid | 20.0 g |
| Sodium chloride | qs. |
| Water | to 1000 mL |

The diluted solution contained Ciprofloxacin in the concentration of 3%, and was adjusted to pH 4.5 with a 2N sodium hydroxide solution.

EXAMPLE 10

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 50.0 g |
| 5-Oxotetrahydrofuran-2-carboxylic acid | 20.0 g |
| Sodium chloride | qs. |
| Water | to 1000 mL |

The diluted solution contained Ciprofloxacin in the concentration of 1%, and was adjusted to pH 4.5 with a 2N sodium hydroxide solution.

EXAMPLE 11

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 50.0 g |
| 5-Oxotetrahydrofuran-2-carboxylic acid | 20.0 g. |
| Sodium chloride | qs. |
| Water | to 1000 mL |

The diluted solution contained Ciprofloxacin in the concentration of 0.2%, and was adjusted to pH 4.5 with a 2N sodium hydroxide solution.

EXAMPLE 12

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 5.0 g |
| 5-Oxotetrahydrofuran-2-carboxylic acid | 2.159 g |
| Sodium chloride | qs. |
| Water | to 100 mL |

The pH of the diluted solution was adjusted to 4.5 with a 2N sodium hydroxide solution.

EXAMPLE 13

An aqueous solution of Ciprofloxacin 5-oxotetrahydrofuran-2-carboxylate was directly prepared from the following ingredients by repeating the same procedures as in Example 4.

| | |
|---|---|
| Ciprofloxacin | 5.0 g |
| 5-Oxotetrahydrofuran-2-carboxylic acid | 2.159 g |
| Sodium chloride | qs. |
| Water | to 100 mL |

The diluted solution contained Ciprofloxacin in the concentration of 3%, and was adjusted to pH 4.5 with a 2N sodium hydroxide solution. =

EXAMPLE 14

An aqueous solution of Ciprofloxacin 5-oxotetrahydrofuran-2-carboxylate was directly prepared from the following ingredients by repeating the same procedures as in Example 4.

| Ciprofloxacin | 5.0 g |
| 5-Oxotetrahydrofuran-2-carboxylic acid | 2.159 g |
| Sodium chloride | qs. |
| Water | to 100 mL |

The diluted solution contained Ciprofloxacin in the concentration of 1%, and was adjusted to pH 4.5 with a 2N sodium hydroxide solution.

EXAMPLE 15

An aqueous solution of Ciprofloxacin 5-oxotetrahydrofuran-2-carboxylate was directly prepared from the following ingredients by repeating the same procedures as in Example 4.

| Ciprofloxacin | 5.0 g |
| 5-Oxotetrahydrofuran-2-carboxylic acid | 2.159 g |
| Sodium chloride | qs. |
| Water | to 100 mL |

The diluted solution contained Ciprofloxacin in the concentration of 0.4%, and was adjusted to pH 4.5 with a 2N sodium hydroxide solution.

EXAMPLE 16

An aqueous solution of Ciprofloxacin 5-oxotetrahydrofuran-2-carboxylate was directly prepared from the following ingredients by repeating the same procedures as in Example 4.

| Ciprofloxacin | 5.0 g |
| 5-Oxotetrahydrofuran-2-carboxylic acid | 2.159 g |
| Sodium chloride | qs. |
| Water | to 2500 mL |

The pH of the diluted solution was adjusted to 4.5 with a 2N sodium hydroxide solution.

EXAMPLE 17

Solubility in Water of Organic Acid Addition Salts of Ciprofloxacin

Ciprofloxacin 5-Oxotetrahydrofuran-2-carboxylate obtained in Examples 1–3 was dissolved in deionized water and an excessive amount of the salt was further added thereto. The resulting suspension was stirred strongly to give a homogeneous solution, and then filtered through a 0.45 micro-membrane filter. The filtrate was subject to high pressure liquid chromatography (HPLC) to determine the amount of the active ingredient in the filtrate.

Separately, the above procedures were repeated with known conventional Ciprofloxacin hydrochloride and lactate for comparison purpose. The results are shown in Table 1 below.

TABLE 1

| Compound | Solubility (mg/mL) |
|---|---|
| Ciprofloxacin 5-oxotetrahydrofuran-2-carboxylate | 180.5 |
| Ciprofloxacin lactate | 107.7 |
| Ciprofloxacin hydrochloride | 26.8 |

From the results, it is confirmed that the organic acid addition salts of Ciprofloxacin according to the invention are superior to other known salts in solubility in water.

EXAMPLE 18

Acute Toxicity

Male mice (weight: about 20 g) were used in this assay. The compound of the invention was intravenously injected into the tail vein of each test mice in various dosages of 500, 400, 350, 300, 250, 200, 150, and 100 mg/kg as Ciprofloxacin. Ciprofloxacin lactate was used as a control compound. Each group which was treated under the same conditions was composed of 10 mice. For 14 days after the injection, the number of dead mice were counted to estimate the value of $LD_{50}$ as Ciprofloxacin. The results are shown in Table 2.

TABLE 2

| Compound | $LD_{50}$ (mg/kg) |
|---|---|
| Ciprofloxacin 5-oxotetrahydrofuran-2-carboxylate | 231.5 |
| Ciprofloxacin lactate | 230.7 |

From the results shown in Table 2, it is confirmed that the organic acid addition salt of Ciprofloxacin according to the invention exhibits acute toxicity similar to that of Ciprofloxacin lactate.

We claim:

1. A compound of the formula:

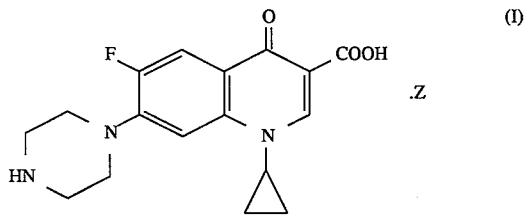

wherein, Z is 5-oxotetrahydrofuran-2-carboxylic acid or 2-hydroxyglutaric acid.

2. A pharmaceutical composition for use in treating infectious diseases caused by bacteria, which comprises the compound of claim 1 as an active ingredient.

3. A method for treating infectious diseases caused by bacteria which comprises administering to the patient an effective amount of the compound of claim 1.

* * * * *